United States Patent [19]

Karrer

[11] 4,234,734
[45] Nov. 18, 1980

[54] 2,2,6,6-TETRAMETHYLPIPERIDINE DERIVATIVES

[75] Inventor: Friedrich Karrer, Zofingen, Switzerland

[73] Assignee: Ciba-Geigy Corporation, Ardsley, N.Y.

[21] Appl. No.: 57,628

[22] Filed: Jul. 16, 1979

[30] Foreign Application Priority Data

Jul. 21, 1978 [CH] Switzerland .................. 7904/78

[51] Int. Cl.³ .................. C07D 401/10; C07D 401/06
[52] U.S. Cl. .................. 546/188; 260/45.8 N; 260/45.8 NT; 546/20
[58] Field of Search .................. 546/20, 188

[56] References Cited

U.S. PATENT DOCUMENTS

| | | | |
|---|---|---|---|
| 3,238,216 | 3/1966 | Janssen | 546/20 |
| 3,940,363 | 2/1976 | Murayama et al. | 546/188 |
| 3,975,462 | 8/1976 | Murayama et al. | 260/45.8 NT |
| 4,005,094 | 1/1977 | Murayama et al. | 260/45.8 N |
| 4,049,647 | 9/1977 | Holt et al. | 546/188 |
| 4,097,587 | 6/1978 | Soma et al. | 260/45.8 A |
| 4,148,783 | 4/1979 | Rasberger et al. | 546/188 |

Primary Examiner—Henry R. Jiles
Assistant Examiner—Robert T. Bond
Attorney, Agent, or Firm—Harry Falber

[57] ABSTRACT

2,2,6,6-Tetramethylpiperidine derivatives of the formula I

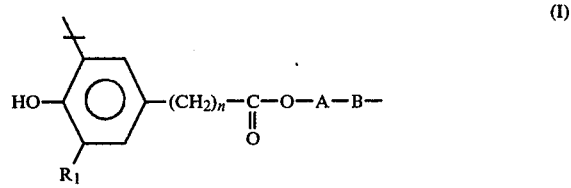

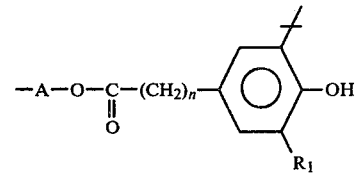

in which A is a radical of the formula II, III or IV, and in formula II B is bonded to the N atom,

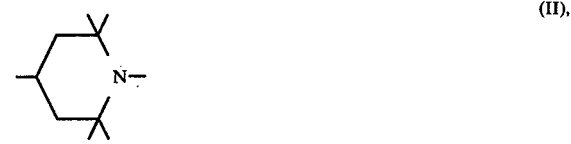

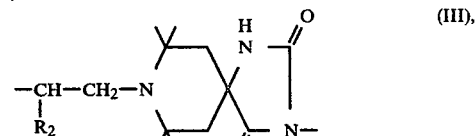

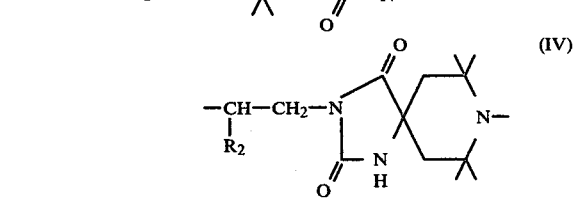

B is $C_2$–$C_{12}$ alkylene, $C_4$–$C_{10}$ alkenylene, $C_6$ alkynylene, xylylene or bitolylene, $R_1$ is H or $C_1$–$C_{12}$ alkyl, $R_2$ is hydrogen, methyl, ethyl, phenyl or phenoxymethyl and n is 0, 1 or 2, for use as stabilizers for synthetic organic polymer.

4 Claims, No Drawings

2,2,6,6-TETRAMETHYLPIPERIDINE DERIVATIVES

The invention relates to novel 2,2,6,6-tetramethyl-piperidine derivatives and also synthetic polymers containing such derivatives as stabilisers.

Piperidine derivatives are known as stabilisers from U.S. Pat. No. 3,940,363, 1,2-bis-(4-benzoyloxy-2,2,6,6-tetramethyl-piperidino)-ethane being cited as compound No. 1 and 1,4-bis-(4-benzoyloxy-2,2,6,6-tetramethyl-piperidino)-trans-2-butene being cited as compound No. 9.

It has now been found that certain 2,2,6,6-tetramethylpiperidine derivatives in which compounds of the above type are linked, for example, to a β-(3,5-di-t-butyl-4-hydroxyphenyl)-propionyloxy radical in the 4-position of the piperidine are particularly advantageous. In addition to an outstanding light stabilising action, such compounds at the same time have a particularly good antioxidant action in synthetic polymers and good processing stability when hot. The derivatives according to the invention are of low volatility, readily compatible with polymers and stable to extraction. In addition, they have outstanding toxicological characteristics.

The invention relates to novel 2,2,6,6-tetramethylpiperidine derivatives of the formula I

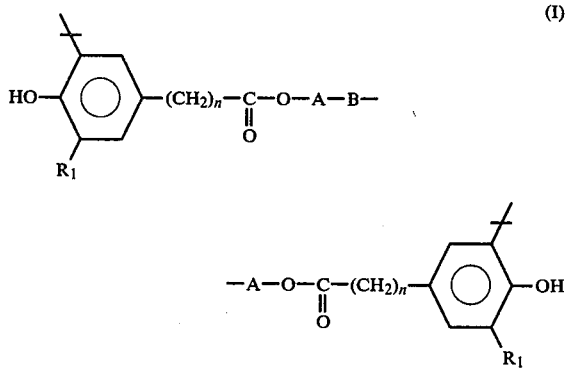

in which A is a radical of the formula II, III or IV, and in formula II B is bonded to the N atom, B is $C_2$–$C_{12}$ alkylene, $C_4$–$C_{10}$ alkenylene, $C_6$ alkynylene, xylylene or bitolylene, $R_1$ is H or $C_1$–$C_{12}$ alkyl, $R_2$ is hydrogen, methyl, ethyl, phenyl or phenoxymethyl and n is 0, 1 or 2.

$C_2$–$C_{12}$ alkylene B is branched or, especially, straight-chain alkylene, in particular having 2–6 C atoms, such as ethylene, 1,3-propylene, 1,4-butylene or hexamethylene, $C_4$–$C_{10}$ alkenylene B is branched or, especially, straight-chain alkenylene, in particular having 4–6 C atoms, such as 1,4-but-2-enylene or 1,6-hex-3-enylene, $C_6$ alkynylene B is especially 1,6-hex-3-ynylene and xylylene B is especially p-xylylene.

$C_1$–$C_{12}$ alkyl $R_1$ is especially alkyl having 1–8 C atoms, such as methyl or tert.-octyl, but in particular tert.-butyl.

Preferred compounds of the formula I are those in which A is a radical of the formula II, B is 1,4-but-2-enylene, p-xylylene or bitolylene, $R_1$ is hydrogen, methyl or tert.-butyl and n is 0, 1 or 2, but in particular 2.

Particularly preferred compounds are those mentioned in the examples.

The derivatives according to the invention can be prepared by methods known per se, for example in the manner described in U.S. Pat. No. 3,940,363 in column 10 et seq., for example by reacting a lower alkyl ester of the formula V

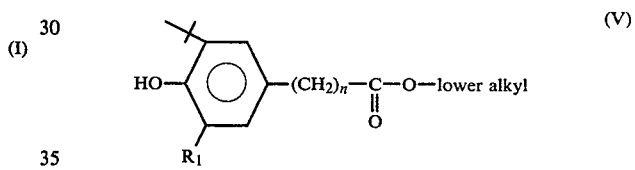

or a corresponding acid chloride or anhydride with a compound of the formula HO—A—B—A—OH.

The trans-esterification can be carried out in a manner known per se, especially in an inert solvent, such as a hydrocarbon, for example xylene or toluene, in the presence of a catalyst, such as a strong base, for example lithium amide, lithium methylate, aluminium iso-propylate, titanium n-butylate, titanium iso-propylate, sodium methylate or sodium ethylate. If desired, an end product which contains a double or triple bond, say in which B is 1,4-but-2-enylene, can subsequently be hydrogenated, for example with hydrogen in the presence of a noble metal catalyst or Raney nickel, for example to give the product in which B is 1,4-butylene. The reaction with an acid chloride is done preferably in the presence of at least 2 Mole equivalents of a base, like a tertiary amine, e.g. triethylamine.

The starting materials are known or, if they are novel, can be obtained by methods known per se.

Thus, for example, 4-hydroxy-2,2,6,6-tetramethyl-piperidine can be reacted with a Hal-B-Hal, in which Hal is chlorine or bromine, preferably in the presence of a base and a solvent at elevated temperature, such as about 50°–160°. Examples of suitable bases are alkali metal carbonates, alkali metal hydroxides or alkali metal oxides. Examples of suitable solvents are ketones, such as acetone, methyl ethyl ketone, diethyl ketone, methyl isobutyl ketone or cyclohexanone, and also dimethylformamide, dimethylsulphoxide or sulpholane. A compound HO—A—B—A—OH in which A has the formula II is obtained in this way and this can then be further reacted in accordance with the procedure indicated above. Analogously, a compound of the formula VI

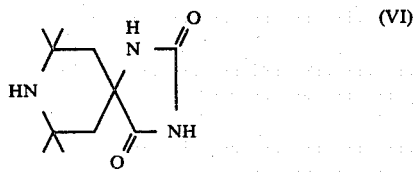

can be reacted with a Hal-B-Hal, as described above, and the product can then be reacted with an oxiranyl-R₂, preferably at elevated temperature and if appropriate under excess pressure, or with a $R_2$—CH(OH)—CH$_2$Br, especially in the presence of a base at elevated temperature, preferably without excess pressure, a compound HO—A—B—A—OH in which A has the formula III being obtained, which can then be further reacted in accordance with the procedure indicated above. Analogously, a compound of the formula VI can first be reacted with an oxiranyl-R₂ or a $R_2$—CH(OH)-CH$_2$Br in accordance with the procedure indicated above and the product can then be reacted with a Hal-B-Hal in accordance with the procedure indicated above. A compound HO—A—B—A—OH in which A has the formula IV is thus obtained and this can then be further reacted in accordance with the procedure indicated above.

According to the present invention, the compounds of the formula I can be used as stabilisers for plastics to prevent their being damaged by the action of oxygen, heat and light. Examples of such plastics are the polymers listed on pages 12–14 of German Offenlegungsschrift No. 2,456,864.

The stabilising of polyolefins and styrene polymers and of polyurethanes is of particular importance and the piperidines of the formula I are outstandingly suitable for this purpose. Examples of such polymers are high density polyethylene and low density polyethylene, polypropylene, ethylene/propylene copolymers, polystyrene, styrene/butadiene/acrylonitrile copolymers, mixtures of polyolefins or of styrene polymers, and polyurethanes based on polyethers or polyesters, in the form of lacquers, elastomers or foams.

The stabilisers are added to the plastics in a concentration of 0.01 to 5% by weight, calculated on the basis of the material to be stabilised. Preferably, 0.03 to 1.5 and particularly preferentially 0.2 to 0.6% by weight of the compounds, calculated on the basis of the material to be stabilised, are incorporated into this material.

Incorporation can take place after polymerisation, for example by mixing the compounds, and if desired further additives, into the melt by the methods customary in the art, before or during shaping, or by applying the compounds, in the form of a solution or dispersion, to the polymer, the solvent subsequently being evaporated if necessary.

The novel compounds can also be added in the form of a master batch, which contains these compounds, for example in a concentration of 2.5 to 25% by weight, to the plastics to be stabilised.

In the case of crosslinked polyethylene, the compounds are added prior to crosslinking.

In addition to the compounds of the formula I, yet further known stabilisers can also be added to the plastics. These stabilisers can be, for example, antioxidants, light stabilisers or metal deactivators, or co-stabilisers, for example of the phosphite type. Furthermore, other additives customary in plastics technology, for example flameproofing agents, antistatic agents, plasticisers, lubricants, blowing agents, pigments, reinforcing substances or fillers can be added. Examples of additives which can be used together with the compounds of the formula I are given on pages 18–24 of German Offenlegungsschrift No. 2,427,853.

The invention therefore also relates to plastics which are stabilised by the addition of 0.01–5% by weight of a compound of the formula I and which, if desired, can also contain further known and conventional additives. The plastics stabilised in this way can be used in very diverse forms, for example in the form of films, fibres, tapes or profiles or as binders or lacquers, adhesives or putties.

The preparation and use of the compounds according to the invention are described in more detail in the following example. Parts and percentages are by weight. The temperatures are given in degrees Centigrade.

EXAMPLE 1

50 ml of xylene were first distilled out of a solution of 36.66 g of 1,4-bis-(2,2,6,6-tetramethyl-4-hydroxypiperidin-1-yl)-but-2-ene (0.1 mol, melting point 208°–210°) and 58.48 g (0.2 mol) of methyl 3-(3,5-di-tert.-butyl-4-hydroxy)-phenyl-propionate in 350 ml of pure xylene (mixture of isomers) under normal pressure through the descending condenser fitted on the reaction vessel (azeotropic removal of the final traces of water). 0.20 g of lithium amide was then added to the reaction mixture and heating was continued, with stirring, the methanol eliminated being continuously slowly distilled out of the reaction mixture. After 2 hours a vapour temperature of 135° was reached (bath temperature 165°). By further slow distillation, the xylene was distilled out from the reaction mixture as completely as possible in the course of 15 hours. No further educts were now detectable in the thin layer chromatogram.

For working up, the viscous residue, which had been cooled to 60°, was dissolved in 300 ml of chloroform, the chloroform solution was washed four times with a little water, dried over sodium sulphate and filtered and the solvent was completely distilled off in vacuo (rotary evaporator). The crude product, which solidifies as crystals after a short time, was twice recrystallised from methyl ethyl ketone/acetonitrile (2:1), by which means colourless, fine crystals of pure 1,4-bis-{2,2,6,6-tetramethyl-4-[3-(3,5-di-tert.-butyl-4-hydroxyphenyl)-propionyloxy]-piperidin-1-yl}-but-2-ene were obtained. The compound has a melting point of 152°–153°.

EXAMPLE 2–9

The following compounds are obtained in a manner analogous to that described in Example 1:

bis-{2,2,6,6-tetramethyl-4-[3-(3,5-di-tert.-butyl-4-hydroxyphenyl)-propionyloxy]-piperidin-1-yl}-p-xylylene (Example 2), m.p. 213°–214°.

bis-{2,2,6,6-tetramethyl-4-[3-(3,5-di-tert.-butyl-4-hydroxyphenyl)-propionyloxy]-piperidin-1-yl}-bitolylene (Example 3), m.p. 134°–135°.

1,4-bis-{2,2,6,6-tetramethyl-4-(3,5-di-tert.-butyl-4-hydroxy-benzoyloxy-piperidinyl-1}-butene-2 (Example 4), m.p. 163°–165°.

bis-{2,2,6,6-tetramethyl-4-(3,5-di-tert.-butyl-4-hydroxybenzoyloxy)-piperidinyl-1}-p-xylylene (Example 5), m.p. 157°–160° and 250°–252° (2 melting points).

1,4-bis-{2,2,6,6-tetramethyl-4-[2-(3,5-di-tert.-butyl-4-hydroxyphenyl)-acetyloxy]-piperidinyl-1}-butene-2 (Example 6), m.p. 207°–209°.

1,4-bis-{2,2,6,6-tetramethyl-4-[3-(3-tert.-butyl-4-hydroxy-5-methylphenyl)-propionyloxy]-piperidinyl-1}-butene-2 (Example 7), m.p. 157°–158°.

bis-{2,2,6,6-tetramethyl-4-[3-(3-tert.-butyl-4-hydroxyphenyl)-propionyloxy]-piperidinyl-1}-p-xylylene (Example 8), m.p. 182°–185°.

1,4-bis-{2,2,6,6-tetramethyl-4-[3-(3,5-di-tert.-butyl-4-hydroxyphenyl)-propionyloxy]-piperidinyl-1}-butane (Example 9), m.p. 162°–164°.

What is claimed is:

1. A 2,2,6,6-tetramethylpiperidine of the formula I

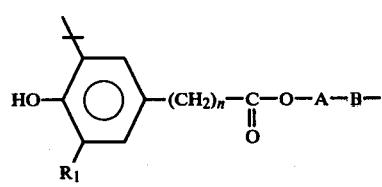  (I)

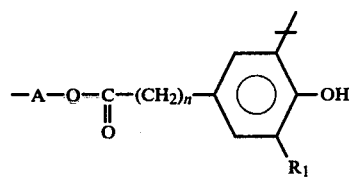

in which A is a radical of the formula II, III or IV, and in formula II B is bonded to the N atom,

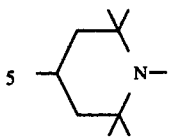  (II),

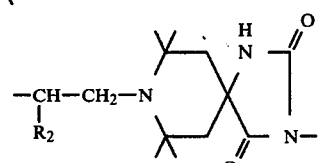  (III),

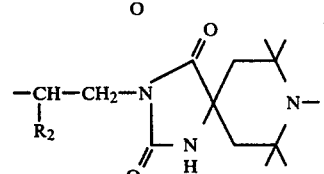  (IV)

B is $C_2$–$C_{12}$ alkylene, $C_4$–$C_{10}$ alkenylene, $C_6$ alkynylene, xylylene or bitolylene, $R_1$ is H or $C_1$–$C_{12}$ alkyl, $R_2$ is hydrogen, methyl, ethyl, phenyl or phenoxymethyl and n is 0, 1 or 2.

2. A compound according to claim 1, in which A is a radical of the formula II, B is 1,4-but-2-enylene, p-xylylene or bitolylene, $R_1$ is hydrogen, methyl or tert.-butyl and n is 0,1 or 2.

3. A compound according to claim 2, in which n is 2.

4. A compound according to claim 1, specifically 1,4-bis-{2,2,6,6-tetramethyl-4-[3-(3,5-di-tert.-butyl-4-hydroxyphenyl)-propionyloxy]-piperidin-1-yl}-but-2-ene.

* * * * *